United States Patent [19]

Ravikumar et al.

[11] Patent Number: 5,571,902

[45] Date of Patent: Nov. 5, 1996

[54] SYNTHESIS OF OLIGONUCLEOTIDES

[75] Inventors: Vasulinga Ravikumar, Carlsbad; Douglas L. Cole, San Diego, both of Calif.

[73] Assignee: ISIS Pharmaceuticals, Inc., Carlsbad, Calif.

[21] Appl. No.: 249,442

[22] Filed: May 26, 1994

Related U.S. Application Data

[63] Continuation-in-part of Ser. No. 99,075, Jul. 29, 1993.

[51] Int. Cl.$^6$ .............................. C07H 1/00; C07H 21/00; C12N 15/11
[52] U.S. Cl. .................. 536/22.1; 536/25.3; 536/25.31; 536/25.33; 536/25.34; 536/25.5; 536/25.6
[58] Field of Search ........................ 536/25.3, 25.34, 536/22.1, 25.33, 25.31, 25.6, 25.5; 556/449

[56] References Cited

U.S. PATENT DOCUMENTS

| | | | |
|---|---|---|---|
| 3,687,808 | 8/1972 | Merigan, Jr. et al. | 195/28 N |
| 4,458,066 | 7/1984 | Caruthers et al. | 536/27 |
| 4,725,677 | 2/1988 | Koster et al. | 536/27 |
| 4,806,463 | 2/1989 | Goodchild et al. | 435/5 |
| 4,845,205 | 7/1989 | Huynh Dinh et al. | 536/28 |
| 5,113,005 | 5/1992 | Celebuski | 556/449 |
| 5,159,095 | 10/1992 | Celebuski | 556/436 |
| 5,264,423 | 11/1993 | Cohen et al. | 514/44 |
| 5,276,019 | 1/1994 | Cohen et al. | 514/44 |

FOREIGN PATENT DOCUMENTS

| | | |
|---|---|---|
| WO91/04983 | 4/1991 | WIPO . |
| WO92/21689 | 6/1992 | WIPO . |

OTHER PUBLICATIONS

Beaucage, S. et al., "Advances in the Synthesis of Oligonucleotides by the Phosphoramidite Approach", *Tetrahedron* 1992, 48(12), 2223–2311.

Burch, R. et al., "Oligonucleotides Antisense to the Interleukin 1 Receptor mRNA Block the Effects of Interleukin 1 in Cultures Murine and Human Fibroblasts and in Mice", *The Journal of Clinical Investigation, Inc.* 1991, 88, 1190–1196.

Celebuski, J. et al, "Synthesis and Utility of a DNA Phosphrylating Agent Based on 2-(Triphenylsilyl)ethanol", *J. Org. Chem.* 1992, 57, 5535–5538.

Higgins, "Medical Sciences", *PNAS USA* 1993, 90, 9903–9905.

Honda, S. et al., "2-Diphenylmethylsilylethyl Group as a New Protecting Group of Internucleotidic Phosphates in Oligonucleotide Synthesis", *Tetrahedron Letters* 1981, 2093–2096.

Iyer, R. et al., "3H-1, 2-Benzodithiole-3-one 1, 1-Dioxide as an Improved Sulfurizing Reagent in the Solid-Phase Synthesis of Oligodeoxyribonucleoside Phosphorothioates", *J. Am. Chem. Soc.* 1990, 112, 1253–1254.

Iyer, R. et al., "The Automated Synthesis of Sulfur–Containing Oligodeoxyribonucleotides Using 3H-1, 2-Benzodithiol-3-one 1,1-Dioxide as a Sulfur-Transfer Reagent", *J. Org. Chem.* 1990, 55(15), 4693–4699.

Kamer, P. et al., "An Efficient Approach Toward the Synthesis of Phosphorothioate Diesters via the Schonberg Reaction", *Tetrahedron Letters* 1989, 30(48), 6757–6760.

Kitajima, I. et al., "Ablation of Transplanted HTLV–I Tax–Transformed Tumors in Mice by Antisense Inhibiton of NF–κB", *Science* 1992, 258, 1792–1795.

March, J., "Advanced Organic Chemistry", pp. 16–18, 237–239, John Wiley & Sons, New York, 1985.

Offensperger, W.–B. et al., "In vivo Inhibition of Duck Hepatitis B Virus Replication and Gene Expression by Phosphorothioate Modified Antisense Oligodoxynucleotides", *The EMBO Journal* 1993, 12(3), 1257–1262.

Rao, M. V. et al., "Dibenzoyl Tetrasulphide –A Rapid Sulphur Transfer Agent in the Synthesis of Phosphorothioate Analogues of Oligonucleotides", *Tetrahedron Letters* 1992, 33(33), 4839–4842.

Simons, M. et al., "Antisense c–myb Oligonucleotides Inhibit Intimal Arterial Smooth Muscle Cell Accumulation in vivo", *Nature* 1992, 359, 67–70.

Streitweiser, Jr., A. et al., "Introduction to Organic Chemistry", pp. 437–440, Macmillan Publishing Co., Inc., New York, 1981.

(List continued on next page.)

Primary Examiner—James O. Wilson
Attorney, Agent, or Firm—Woodcock Washburn Kurtz Mackiewicz & Norris

[57] ABSTRACT

Synthetic processes are provided for the solution phase synthesis of oligonucleotides, especially phosphorothioate oligonucleotides, and intermediate compounds useful in the processes. Intermediates having structure

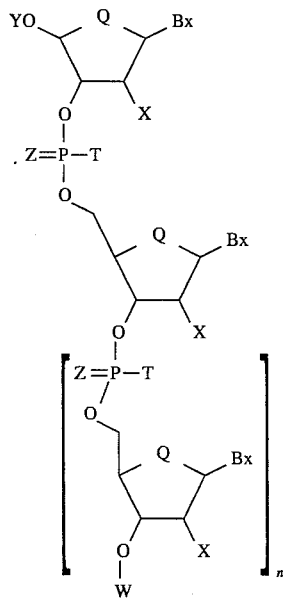

are prepared in accord with preferred embodiments.

16 Claims, 3 Drawing Sheets

OTHER PUBLICATIONS

Takaku, H. et al., "Use of 1,1,1,3,3,3,-Hexafluoro-2-Propyl Protecting Group in the Synthesis of DNA Fragments via Phosphoramidite Intermediates", *Tetrahedron Letters* 1988, 29(1), 81-84.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letters* 1991, 32(26), 3005-3008.

Vlassov, V., "Inhibition of Tick-Borne Viral Encephalitis Expression Using Covalently Linked Oligonucleotide Analogs", in Oligodeoxynucleotides as Antisense Inhibitors of Gene Expression: Therapeutic Implications, Jun. 18-21, 1989, Sheraton Potomac Inn, Rockville, MD.

Wright, P. et al., "Large Scale Synthesis of Oligonucleotides via Phosphoramidite Nucleosides and a High-loaded Polystyrene Support", *Tetrahedron Letters* 1993, 34(21), 3373-3376.

Wolter, A., et al., "Polymer Support Oligonucleotide Synthesis XX: Sysnthesis of Henhectacosa Deoxynucleotide by Use of a Dimeric Phosophoramidite Synthon", *Nucleosides & Nucleotides* 1986, 5(1), 65-77.

Bannwarth, W., "Synthesis of Oligodeoxynucleotides by the Phosphite-Triester Method Using Dimer Units and Different Phosphorous-Protecting Groups", *Helvetica Chimica Acta*.

Miura, K. et al., "Blockwise MEchanical Synthesis of Oligonucleotides by the Phosphoramidite Method", *Chem. Pharm. Bull.* 1987, 35(2), 833-836.

Kumar, G. et al., "Improvements in Oligodeoxyribonucleotide Synthesis: Methyl N,N-Dialkylphosphoramidite Dimer Units for Solid Support Phosphite Methodology", *J. Org. Chem.* 1984, 49, 4905-4912.

Wyatt, J. et al, "Combinatorially Selected Guanosine-Quartet Structure is a Potent Inhibitor of Human Immunodeficiency Virus Envelope-Mediated Cell Fusion", *PNAS USA* 1994, 91, 1356-1360.

SYNTHESIS OF OLIGONUCLEOTIDES

CROSS-REFERENCE TO RELATED APPLICATIONS

This application is a continuation in part of U.S. Ser. No. 08/099,075 filed Jul. 29, 1993, assigned to the assignee of this invention.

FIELD OF THE INVENTION

This invention is directed to processes for synthesizing oligonucleotides, especially phosphorothioate oligonucleotides, and to intermediates used in that process. This invention is drawn to solution phase syntheses having improved efficiencies and enhanced convenience and cost.

BACKGROUND OF THE INVENTION

Oligonucleotides are important materials for research, diagnostic, therapeutic and other purposes. An ever-growing demand for improved oligonucleotides, oligonucleotide analogs and for methods for their preparation and use has arisen. For example, oligonucleotides are widely used in genomic research as probes, primers and a wide array of other research uses. One widely used technique that uses oligonucleotides primers is PCR (polymerase chain reaction) amplification.

Oligonucleotides are also useful in diagnostics since they can specifically hybridize to nucleic acids of interest in the etiology of disease. Oligonucleotides are currently in clinical trials as therapeutic moieties in the treatment of disease states. For example, workers in the field have now identified oligonucleotide compositions that are capable of modulating expression of genes implicated in viral, fungal and metabolic diseases. In short, oligonucleotides are important molecules having a large commercial impact in biotechnology and medicine. Improved methods for the synthesis of oligonucleotides are in demand, especially methods which have improvements in cost and convenience.

The current methods of choice for the preparation of phosphorothioate oligonucleotides employ solid-phase synthesis wherein an oligonucleotide is prepared on a polymer or other solid support. Solid-phase synthesis relies on sequential addition of nucleotides to one end of a growing oligonucleotide. Typically, a first nucleoside is attached to an appropriate support, e.g. glass, and nucleotide precursors, typically phosphoramidites, are added stepwise to elongate the growing oligonucleotide. The nucleotide phosphoramidites are conventionally reacted with the growing oligonucleotide using the principles of a "fluidized bed" for mixing of the reagents. The silica supports suitable for anchoring the oligonucleotide are very fragile and thus can not be exposed to aggressive mixing.

In these and other solid-phase procedures the oligonucleotide is synthesized as an elongating strand. However, the number of individual strands that can be anchored to a unit surface area of the support is limited. Also, the commercially available activated nucleotides that are presently used to add to a growing oligonucleotide are relatively expensive and must be used in stoichiometric excess. Also, the activating agents, e.g. tetrazole, are used in large excess.

The chemical literature discloses numerous processes for coupling nucleosides through phosphorous-containing covalent linkages to produce oligonucleotides of defined sequence. One of the most popular processes is the phosphoramidite technique (see, e.g., Beaucage, et al., *Tetrahedron* 1992, 48, 2223 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The phosphoramidite technique, however, is not without its disadvantages. For example, cyanoethyl phosphoramidite monomer is quite expensive. Although considerable quantities of monomer go unreacted in a typical phosphoramidite coupling, unreacted monomer can be recovered, if at all, only with great difficulty. Also, acrylonitrile, the by-product of deprotection of the cyanoethoxy group on the phosphate group is carcinogenic and in some cases acts as a Michael acceptor to form undesired side-products.

Other exemplary solid state synthetic schemes are set forth in U.S. Pat. Nos. 34,069 Koster et al.; and 5,132,418 Carruthers et al..

While currently utilized solid phase syntheses are useful for preparing small quantities of oligonucleotide, they typically are not amenable to the preparation of large quantities of oligonucleotides necessary for biophysical studies, preclinical and clinical trials and commercial production. Moreover, such synthetic procedures are very expensive. Thus, although there is a great demand for oligonucleotides, especially phosphorothioate oligonucleotides, the art suggests no large scale techniques for their preparation. Accordingly, there remains a long-felt need for such methods and for intermediates useful in such methods.

SUMMARY OF THE INVENTION

Figure 1:
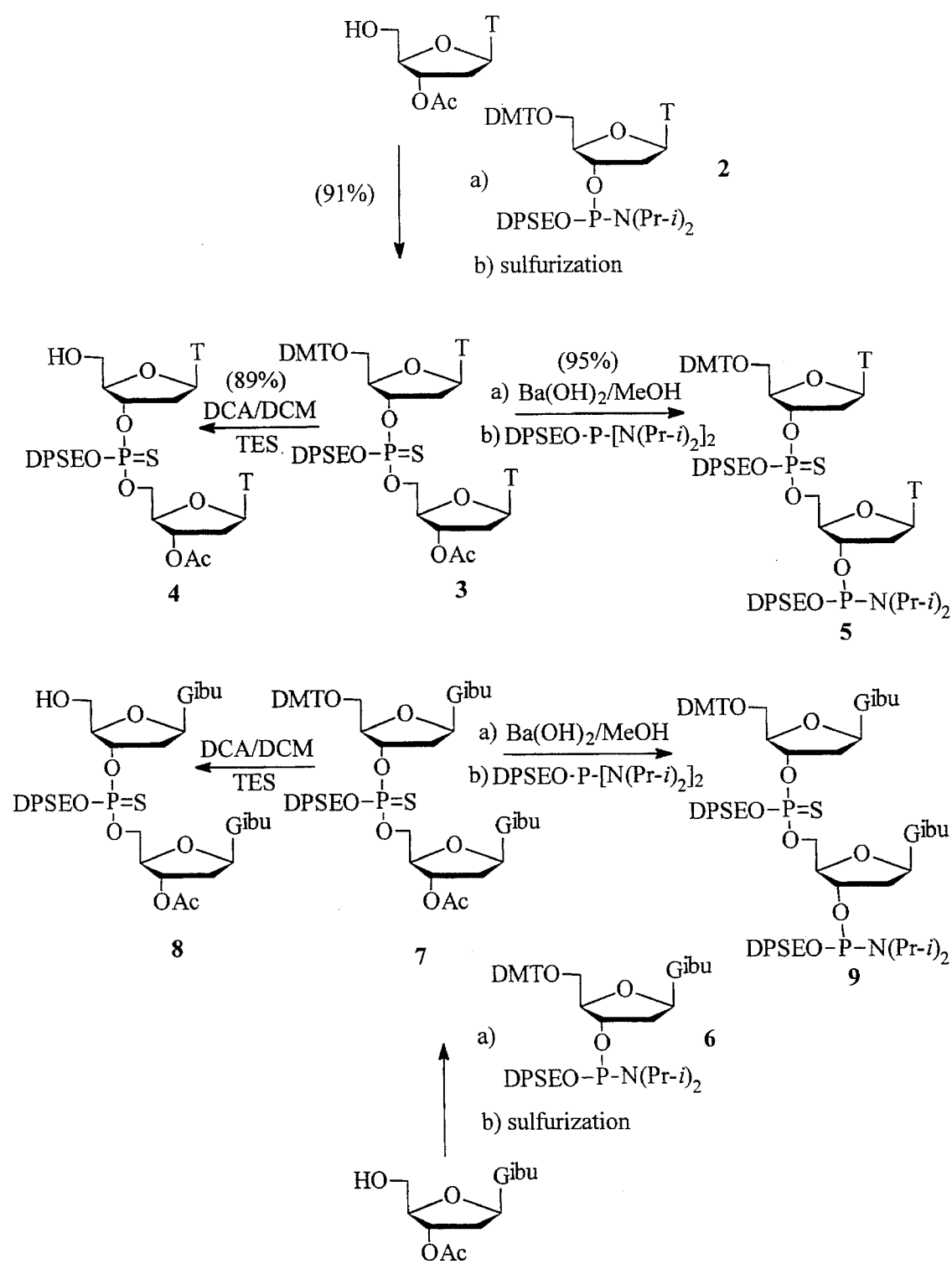
FIG. 1 is a reaction schematic depicting exemplary routes for the syntheses of intermediates useful in the practice of the invention.

In accordance with the invention, methods are provided for the synthesis of oligonucleotide moieties. A first synthon, having the structure

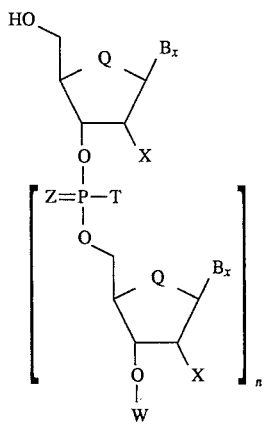

is caused to react with a second synthon having the structure

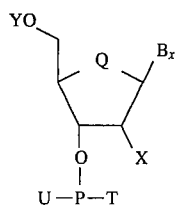

to form a moiety having the structure

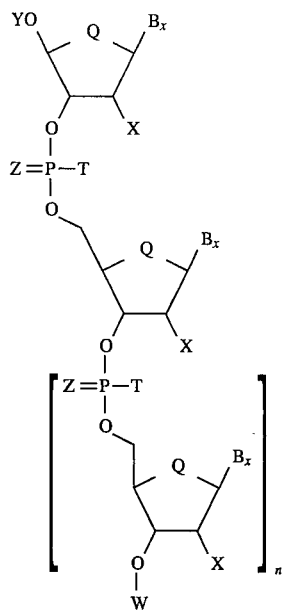

Wherein each Q is independently O, S, $CH_2$, CHF or $CF_2$. In accordance with embodiments of the invention, each $B_x$ is independently a nucleosidic base; each X is independently, OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O-, S-, or N-alkyl; O-, S-, or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide; Y is a 5'= hydroxyl protecting group; W is a 3' hydroxyl protecting group; each Z is O or S; T is a phosphorous blocking group; U is a phosphite activating group; and n is an integer from 0 to 50.

In accordance with preferred embodiments, each group T can be a silylalkoxy group wherein the Si atom of this group includes three substituent R groups thereon. Preferably these R groups, independently, are alkyl or aryl with methyl, t-butyl and phenyl being most preferred. U can be a dialkylamino group. In another preferred embodiment, the first synthon is formed by coupling of a 3' hydroxyl protected nucleoside with a 5' protected nucleoside through a phosphite linkage.

In yet other preferred embodiments, the processes of the invention are accomplished such that the second synthon is prepared via reaction of a precursor nucleoside with a reagent $[R_1R_2N]_2PO(CH_2)_xSiR_3R_4R_5$ wherein $R_1$ and $R_2$ independently are alkyl having 1 to about 10 carbon atoms, $R_3$, $R_4$, and $R_5$ are, independently, alkyl having 1 to about 10 carbon atoms or aryl having 6 to about 10 carbons atoms, and x is 1 to about 7. Useful as the precursor nucleoside for the preparation of such a second synthon is a nucleoside that corresponds in structure to the second synthon above, except it bears a hydrogen atom on it 3' hydroxyl group in place of the U—P—T groups. Preferably this reaction is conducted in the presence of 1H-Tetrazole, 5-(4-Nitrophenyl)-1H-tetrazole, or diisopropylammonium tetrazolide.

It is also preferred that the processes further comprise removing the groups W, T, and Y from the moiety and oxidizing the moiety to form either phosphorothioate or phosphodiester bonds.

The processes of the invention may be performed iteratively such that the product resulting from a first reaction sequence is transformed into a "new" first synthon for iterative reaction with a further second synthon by removal of the Y group. The processes of the invention my further be preformed iteratively such that the product resulting from a first reaction sequence is transformed into a "new" second synthon for iterative reaction with a further first synthon by removal of the W group followed by phosphitation. While solution phase reactions are preferred in the practice of this invention, in iterative processes and otherwise, one of the "new" second synthons of the above process, as described in the preceding sentence, can be used in the place of a standard mono-nucleotide phosphoramidite synthon in a standard solid phase reaction to elongated an growing oligonucleotide on a solid phase support. Thus instead of adding just a single nucleotide at a time as is practiced in current solid phase synthesis technology, dimers, trimers, tetramers and even high homologues can be advantageously linked to a growing oligonucleotide on a solid support. Such dimers, trimers, tetramers and high homologues are prepared using the processes of the invention and then are carried over and used in place of the standard phosphoamidites of currently practiced solid phase oligonucleotide synthesis.

In accordance with other embodiments of the invention, there are reacted together, in solution, a first synthon comprising at least two nucleoside units having a 5' location protected with a 5' hydroxylic blocking group and a 3' location substituted with a function having the formula

wherein U is a phosphite activating group and T is a phosphorous blocking group, with a second synthon comprising a nucleoside unit having a 3' location protected with a 3' hydroxylic blocking group and a 5' location capable of reacting with the U—P—T function. It is preferred that the product of the reaction be oxidized to form either phosphodiester or phosphorothioate internucleoside bonds. It is also preferred for some embodiments that the second synthon comprise at least two nucleoside units.

In other preferred methodologies, the function U—P—T is incorporated through reaction with a reagent $[R_1R_2N]_2PO(CH_2)_x SiR_3R_4R_5$ wherein $R_1$ and $R_2$ independently are alkyl having 1 to about 10 carbon atoms, $R_3$, $R_4$, and $R_5$ are, independently, alkyl having 1 to about 10 carbon atoms or aryl having 6 to about 10 carbons atoms, and x is 1 to about 7.

In other aspects of the invention, compounds are provided having the formulas

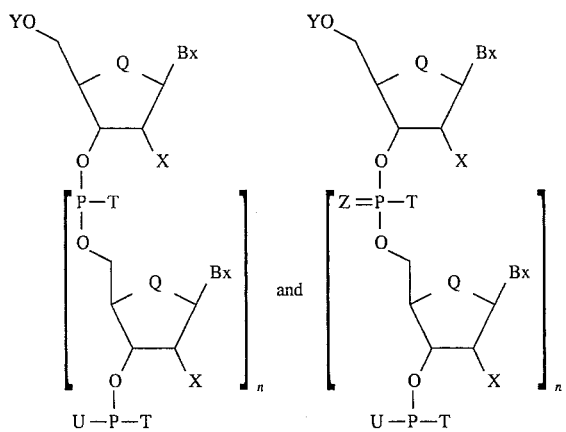

Where each Q is, independently O, S, $CH_2$, CHF or $CF_2$. In such compounds, each $B_x$ is independently a nucleosidic base; each X is independently, OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide; each Z is independently O or S; Y is H or a hydroxyl protecting group; U is a phosphite activating group; each T is independently a phosphorous blocking group; and n is an integer from 1 to 50.

In accordance with other embodiments of the invention, the phosphorous blocking group has the formula— $O(CH_2)_xSiR_3R_4R_5$ wherein $R_3$, $R_4$, and $R_5$ are, independently, alkyl having 1 to about 10 carbon atoms or aryl having 6 to about 10 carbons atoms, and x is 1 to about 7.

It is a significant aspect of the present invention that libraries of oligomers can be constructed and stored to facilitate the synthesis and identification of useful oligonucleotides. Accordingly, the invention is directed to libraries comprising a plurality of compounds in accordance with the foregoing formulas and to oligonucleotides synthesized therefrom.

DETAILED DESCRIPTION OF PREFERRED EMBODIMENTS

This invention provides new and improved processes for the preparation of phosphorous-containing covalent linkages and intermediates useful in such processes. Utilizing these processes and intermediates, phosphodiester and phosphorothioate oligonucleotides are prepared from a plurality of nucleoside or oligonucleotide subunits. The nucleoside subunits may be "natural" or "synthetic" moieties. Thus, in the context of this invention, the term "oligonucleotide" in a first instance refers to a polynucleotide formed from a plurality of linked nucleoside units. The nucleosides are formed from naturally occurring bases and pentofuranosyl sugar groups. The term "oligonucleotide" thus effectively includes naturally occurring species or synthetic species formed from naturally occurring subunits.

The present invention provides processes for the efficient synthesis of the oligonucleotides and modified oligonucleotide compounds (analogs). In preferred embodiments, certain products of the invention are prepared by processes that comprise contacting a protected nucleoside having formula I, i.e. a precursor nucleoside, with a phosphitylation reagent having the formula $(R_1R_2N)_2PO(CH_2)_xSiR_3R_4R_5$ for a time and under reaction conditions effective to form a silylalkyl phosphoramidite monomer having formula II

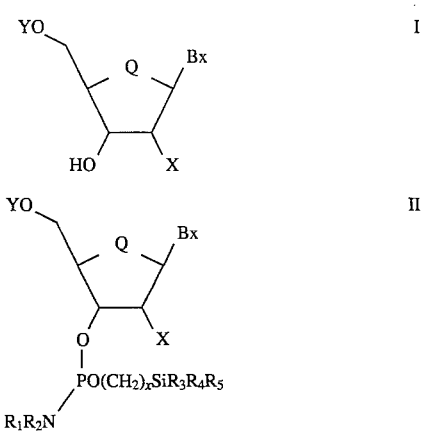

wherein:

each Q is, independently, O, S, $CH_2$, CHF or $CF_2$;

each $B_x$ is, independently, a nucleosidic base;

each X is, independently, OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide;

Y is a 5' hydroxyl protecting group;

$R_1$ and $R_2$, independently, are alkyl having 1 to about 10 carbon atoms;

$R_3$, $R_4$, and $R_5$ are, independently, alkyl having 1 to about 10 carbon atoms or aryl having 6 to about 10 carbons atoms; and x is 1 to about 7.

Monomers of formula II then are contacted with a 3' hydroxyl protected nucleoside having formula III for a time and under reaction conditions effective to form dimers having formula IV

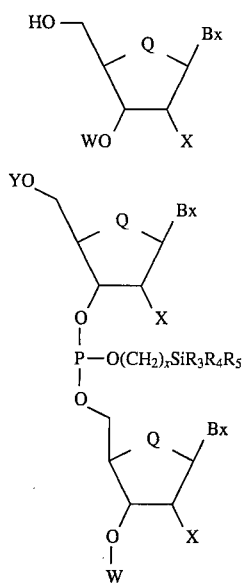

III

IV where W is a 3' hydroxyl protecting group and Y is a 5' hydroxyl protecting group and $R_3$, $R_4$ and $R_5$ are defined as above.

A dimer having formula IV is then contacted with an oxidizing agent for a time and under reaction conditions effective to form oxidation products having formula V (where Z=O or S and n=1). The dimer of formula V can be converted into a dimeric synthon analogous to either the monomeric synthon of structure II or to the monomeric synthon of structure III. Alternatively subsequently reaction of the dimeric compound of structure V with fluoride ion in the conventional manner gives either a phosphodieser or phosphorothioate moiety having formula VI.

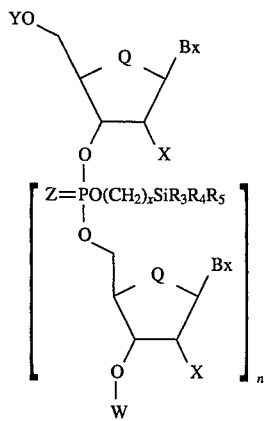

V

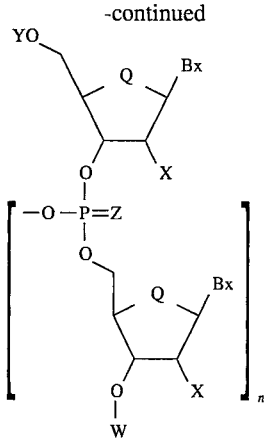

VI

For conversion of the dimer of formula V (where n is 1) to a dimeric synthon analogous to that of structure III above, the 5' hydroxy blocking group Y is removed in a conventional manner to yield a compound of formula VII. This compound is then subsequently contacted with a further phosphitylated nucleoside of formula II under reaction conditions effective to form trimers of formula VIII.

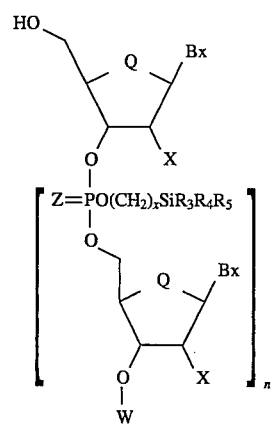

VII

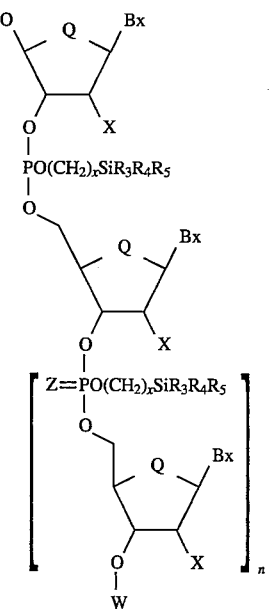

VIII

Trimers having formula VIII are then contacted with an oxidizing agent for a time and under reaction conditions effective to form oxidation products having formula V (where n is increased by one). If a trimeric product is desired, the trimer of formual V is deblocked such as with the conventional fluoride ion or by the use of tetrafluorosilane in a "wet" solvent to produce either a phosphodiester or phorphorothioate moiety having formula VI. If higher homologues are desired, the trimer of formula VIII can be deblocked at the 5' position removing the Y hydroxyl protecting group to yield a synthon analogues to formula VII or deblocked at the 3' position removing the W hydroxyl protecting group and phosphitylated to yield a timeric synthon analogous to the compound of formula II. Thus a library of building blocks of various lengths can be formed. Units can be added together as monomers, as dimers, as trimers, etc, for the preparation of higher homologues.

In other embodiments of the present invention, compounds of formula I are contacted with other suitable coupling reagents to form monomers of formula IIa, wherein U is a phosphite activating group, and T is a phosphorous blocking group. Monomers of formula IIa then are contacted with 3' hydroxyl protected nucleoside having formula III for a time and under reaction conditions effective to form dimers having formula IVa.

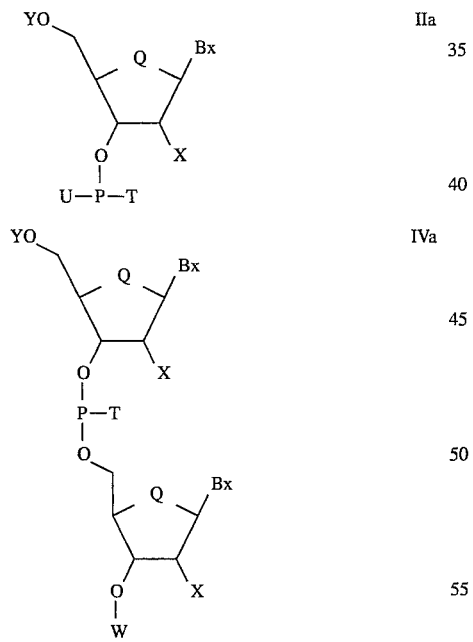

where W is a 3" hydroxyl protecting group, Y is a 5' hydroxyl protecting group and T is a phosphorous protecting group.

A dimer having formula IVa is then contacted with an oxidizing agent for a time and under reaction conditions effective to form oxidation products having formula Va (where Z=O or S and n=1).

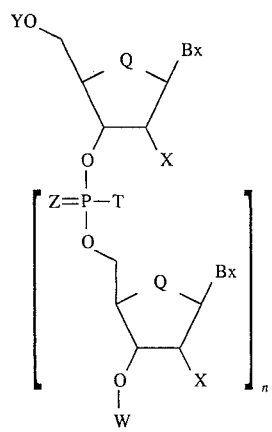

A dimer of formula Va can also be reacted conventionally to remove 5' hydroxy blocking group Y to yield a compound of formula VIIa (where n is 1) and subsequently contacted with a further phosphitylated nucleoside of formula II under reaction conditions effective to form trimers of formula VIIIa.

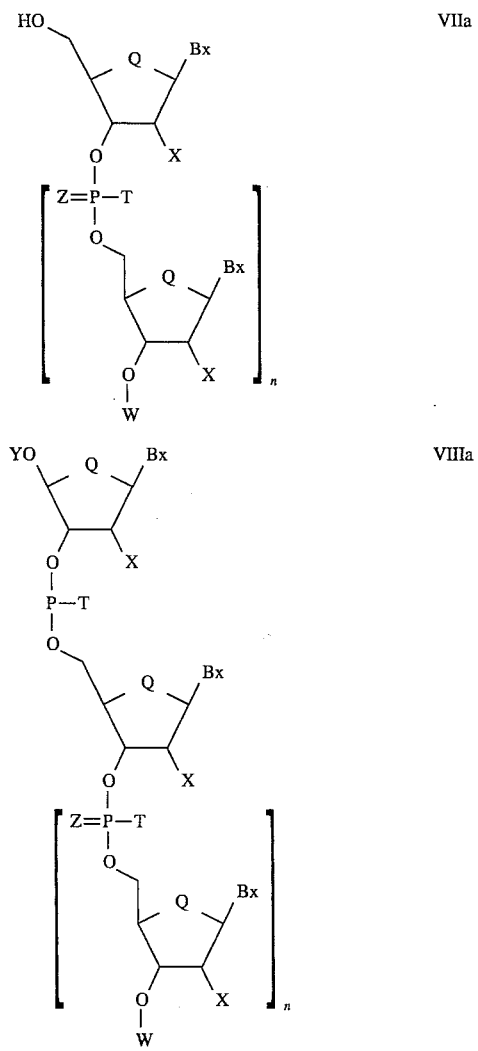

Trimers having formula VIIIa are then contacted with an oxidizing agent for a time and under reaction conditions effective to form oxidation products having formula Va (where n is increased by one). This cycle is repeated to give the length of the desired product. If such product is the final product it is subsequently reacted such as with the conventional fluoride ion or tetrafluorosilane in a "wet" solvent to produce either a phosphodiester or phosphorothioate moiety having formula VI.

Oligonucleotides of formula Va can also be converted to higher analogues corresponding to phosphitylated nucleosides of formula II, above. To form such compounds a dimer of formula Va (n=1) is deprotected at its 3' hydroxyl by removal of the group W and phosphitylated to yield a dimer of formula Vb. The compound of formula Vb can be reacted with a compound of formula VIIa to form a new compound Vc, having one phosphite linking group located between the portion obtained from the compound of formula Vb and the portion obtained from the compound of formula VIIa.

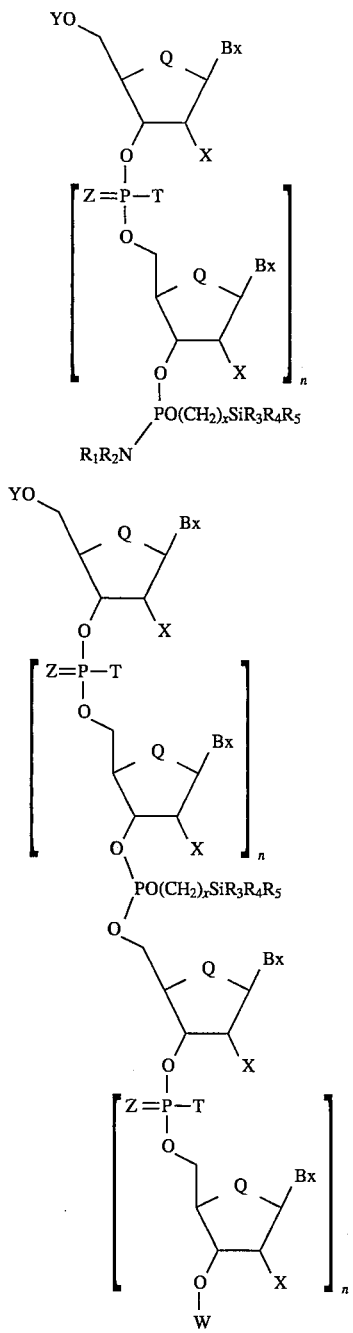

Subsequent oxidization of the phosphite linkage in Vc to a phosphate linkages yields a new compound of formula Va where n is the total of the n units from both the compound of formula VIIa and the compound of formula Vb.

Oligonucleotides according to the invention also can include modified subunits. Representative modifications include modification of a heterocyclic base portion of a nucleoside or a sugar portion of a nucleoside. Exemplary modifications are disclosed in the following U.S. patent application Ser. No. 463,358, filed Jan. 11, 1990, entitled "Compositions And Methods For Detecting And Modulating RNA Activity; Ser. No. 566,977, filed Aug. 13, 1990, entitled "Sugar Modified Oligonucleotides That Detect And Modulate Gene Expression; Ser. No. 558,663, filed Jul. 27, 1990, entitled "Novel Polyamine Conjugated Oligonucleotides"; Ser. No. 558,806, filed Jul. 27, 1991, entitled "Nuclease Resistant Pyrimidine Modified Oligonucleotides That Detect And Modulate Gene Expression"; and Ser. No. PCT/US91/00243, filed Jan. 11, 1991, entitled "Compositions and Methods For Detecting And Modulating RNA Activity". Each of these patent applications are assigned to the assignee of this invention. The disclosure of each is incorporated herein by reference.

The term oligonucleotide thus refers to structures that include modified portions, be they modified sugar moieties or modified base moieties, that function similarly to natural bases and natural sugars. Representative modified bases include deaza or aza purines and pyrimidine used in place of natural purine and pyrimidine bases; pyrimidine having substituent groups at the 5 or 6 position; purines having altered or replacement substituent groups at the 2, 6, or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

In certain embodiments, the compounds of the invention include conjugate groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, phospholipids, biotin, phenanthroline, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. patent application Ser. No. 116,801, filed Sep. 3, 1993, and U.S. Pat. No. 5,218,105. Each of the foregoing is commonly assigned with this application. The entire disclosure of each is incorporated herein by reference.

Altered base moieties or altered sugar moieties also include other modifications consistent with the spirit of this invention. Such oligonucleosides are best described as moieties that are structurally distinguishable from yet functionally interchangeable with naturally occurring or synthetic wild type oligonucleotides. All such oligonucleotides are comprehended by this invention so long as they function effectively to mimic the structure of a desired RNA or DNA strand.

Oligonucleotides prepared via the process and intermediates of the invention can be used as primers for enzymes which polymerize nucleotides, for example, polymerases and reverse transcriptases, such as in the well-known PCR technology. Oligonucleotides can also be used as probes for specific oligonucleotide sequences. Conventional methods for use of oligonucleotides as probes are disclosed in, for example, "Molecular Cloning; A Laboratory Manual" 2d. Ed., J. Sambrook et al., Cold Spring Harbor Press, at chapter 10 and the references therein, which are hereby incorporated by reference.

While compounds of the invention as small as dimeric units are useful, preferred the olignucleotides of the invention comprise from about 10 to about 30 subunits, although oligomers of up to 50 or even several hundred subunits may be useful. It is more preferred that such oligonucleotides comprise from about 15 to 25 subunits. As will be appreciated, a subunit is a base and sugar combination suitably bound to adjacent subunits through a phosphorous-containing linkage. When used as "building blocks" in assembling oligonucleotides, even smaller assemblies are preferred. The smallest, a dinucleotide assembly, is two nucleotide linked by a protected phosphorothioate or phosphodiester linkage.

One use of oligonucleotides is in targeting RNA or DNA. One specific such use is targeting of RNA or DNA that can code for protein. It is preferred that the RNA or DNA portion which is targeted using the oligonucleotide be preselected to comprise that portion of DNA or RNA which codes for the protein whose formation or activity is to be modulated. The targeting portion of the composition to be employed is, thus, selected to be complementary to the preselected portion of DNA or RNA. Such use that is to be an antisense oligonucleotide for that portion.

In accordance with one preferred embodiment of this invention, a compound described as Oligonucleotide 5320 having the structure $T_2G_4T_2$ can be prepared using the process and intermediates of the invention. The synthesis of this compound is shown in the FIGS. 1, 2 and 3 of this specification. As is described in the "Abstract" section of Wyatt, et al., *Proc. Natl. Acad. Sci.*, 1994, 91, 1356–1360, "The phosphorothioate oligonucleotide $T_2G_4T_2$ was identified as an inhibitor of HIV infection in vitro. . . "Other preferred compounds having complementary sequences for herpes, papilloma and other viruses can also be prepared utilizing the process of the invention.

Oligonucleotides are also used as research reagents. For example, phosphorothioate oligonucleotides have been utilized in the studies of enzyme biochemistry and protein-nucleic acid interactions. These and other applications of phosphorothioate oligonucleotides are listed in "Oligonucleotides and Analogues A Practical Approach", F. Eckstein Ed., IRL Press, at pages 88–91, and in the references contained therein, which are hereby incorporated by reference.

In one aspect, the present invention is directed to synthetic methods wherein a protected nucleoside having formula I is contacted with a coupling reagent such as one having the formula $(R_1R_2N)_2PO(CH_2)_xSiR_3R_4R_5$ for a time and under conditions effective to form a silylalkyl phosphoramidite monomer having formula II.

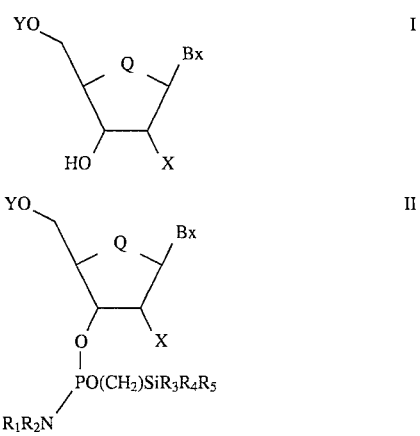

Such contacting preferably is effected under anhydrous conditions in the presence of a weak acid like 1H-tetrazole or 5-(4-nitrophenyl)-1H-tetrazole or diisopropylammonium tetrazolide or any other acid.

Q can be S, $CH_2$, CHF $CF_2$ or, preferably, O. In a further preferred group of compounds, Q is S (see, e.g., Secrist, et al., Abstract 21, Synthesis and Biological Activity of 4'-Thionucleosides, Program & Abstracts, Tenth International Roundtable, Nucleosides, Nucleotides and their Biological Applications, Park City, Utah, Sep. 16–20, 1992). Each Q is independently selected and, hence, can be the same as or different from other Q within a given compound.

$B_x$ can be nucleosidic bases selected from the natural nucleosidic bases adenine, guanine, uracil, thymine, cytosine as well as other bases including 2-aminoadenosine or 5-methylcytosine. In addition, other non-naturally occurring species can be employed to provide stable duplex or triplex formation with, for example, DNA. Representative bases are disclosed in U.S. Pat. No. 3,687,808 (Merigan et al.) which is incorporated herein by reference.

X can be OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O-, S-, or N-alkyl; O-, S-, or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide. It is intended that the term "alkyl" denote branched and straight chain hydrocarbon residues, including alkyl groups having one or more $^3H$ and/or $^{14}C$ atoms. It is preferred that X is H or OH, or, alternatively F, O-alkyl or O-alkenyl, especially where Q is O. Preferred alkyl and alkenyl groups have from 1 to about 10 carbon atoms.

Representative 2'-O-substituted oligonucleotides are described in PCT patent application WO 93/13121, filed Dec. 23, 1992, entitled Gapped 2' Modified Phosphorothioate Oligonucleotides, and U.S. patent application Ser. No. US93/06807 filed Jul. 20, 1993 entitled Novel 2'-O-Alkyl Nucleosides and Phosphoramidites Processes for the Preparation and Uses Thereof and in the references within these applications. Both applications are assigned to the same assignee as this application, and are hereby incorporated by reference.

For example, in the above cited references 2'-O-substituted nucleosides are disclosed, including 2'-O-alkyl (methyl through octadecyl); -allyl, -dimethylallyl, -(N-phthalimido)prop-3-yl and -(N-phthalimido) pent-3-yl; -(imidazol-1-yl)butyl; and -pentyl-w-(N-phthalimido). Other substitutent groups disclosed in the references as useful for substitution at the 2' position of nucleosides include fluoro, C1–C9 aminoalkoxy; C1–C9 alkylimidazole, and polyethyleneglycol.

Y can be any hydroxyl protecting group for the 5' hydroxyl function of nucleosides. Preferably, Y is stable under basic conditions but can be removed under acidic conditions. A wide variety of protecting groups can be employed in the methods of the invention. In general, protecting groups render chemical functionality inert to specific reaction conditions, and can be appended to and removed from such functionality in a molecule. Representative protecting groups are disclosed by Beaucage, S. L.; Uyer, R. P., Advances in the Synthesis of Oligonucleotides by the Phosphoramidite Approach, Tetrahedron, 1992, 48, 2223–2311. Preferred protecting groups include dimethoxytrityl (DMTr), monomethoxytrityl, 9-phenylxanthen-9-yl (Pixyl) and 9-(p-methoxyphenyl)xanthen-9-yl (Mox).

Coupling reagents preferably have the formula $(R_1R_2N)_2PO(CH_2)_xSiR_3R_4R_5$ where $R_1$ and $R_2$ independently are alkyl having 1 to about 10 carbon atoms, $R_3$, $R_4$, and $R_5$ are, independently, alkyl having 1 to about 10 carbon atoms or aryl having 6 to about 10 carbons atoms, and x is 1 to about 7. These are preferably prepared by reacting an alcohol having formula $HO(CH_2)_xSiR_3R_4R_5$ with phosphorus trichloride and reacting the resultant product, $CL_2PO(CH_2)_xSiR_3R_4R_5$, with at least two equivalents of an amine having formula $R_1R_2NH$. The ammoniacal R groups can be the same or different and may be alkyl having 1 to about 10 carbon atoms, preferably 1 to 6 carbon atoms, more preferably 3 carbon atoms. Isopropyl groups are particularly preferred. The silyl R groups can be the same or different and may be alkyl having 1 to about 10 carbon atoms or aryl having 6 to about 10 carbon atoms. Preferably, $R_3$, $R_4$ and $R_5$ are selected from ethyl, ethyl, isopropyl, propenyl, n-butyl, t-butyl, and phenyl groups. Preferably, two of these silyl R groups are phenyl groups and one is a methyl group.

In the formula of the above coupling groups, the variable x can be 1 to about 7, preferably 1 to about 4, more preferably 2. A number of suitable alcohols are disclosed by U.S. Pat. No. 5,159,095, issued Oct. 27, 1992 in the name of Celebuski, which is incorporated herein by reference. One preferred coupling reagent is diphenylmethylsilylethyl N,N-diisopropylphosphoramidite, which can be derived from diphenylmethylsilylethyl alcohol via diphenylmethylsilylethyl phosphodichloridite.

Silylalkyl phosphoramidite monomers having formula II can be contacted with 3'-hydroxyl protected nucleosides having formula III for a time and under conditions effective to form phosphite dimers having formula IV, where the group W is a 3' hydroxyl protecting group.

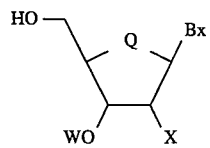

III

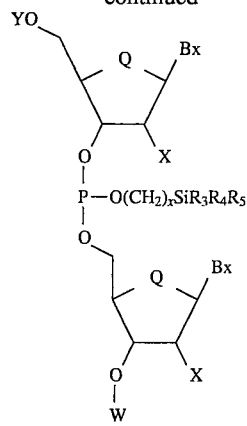

IV

In preferred embodiments, such contact is effected under anhydrous conditions in the presence of an activating agent such as 1H-tetrazole, 5-(4-nitrophenyl)-1H-tetrazole, or diisopropylammonium tetrazolide.

W can be any hydroxyl protecting group for the 3' hydroxyl function of nucleosides. Preferably, W is stable under acidic conditions but can be removed under basic conditions. A wide variety of protecting groups can be employed in the methods of the invention. Preferred protecting groups include acyl protecting groups. A particularly preferred acyl group is acetyl. Other useful blocking groups that are stable under acid conditions but that can otherwise be removed are as is described in Beaucage et al., ibid.

Protecting groups for the compounds of the invention are selected such that the 3'-hydroxyl terminus protecting group W and the 5'-hydroxyl terminus protecting group Y are removed under different conditions. Protecting groups for the phosphite moiety, for example the—$O(CH_2)xSiR_3R_4R_5$ group of compounds of formula II, are chosen such that they are stable to conditions required for the removal of either the 3'-hydroxyl terminus protecting group W or the 5'-hydroxyl terminus protecting group Y. Protecting groups for nucleobases are chosen such that they are stable to conditions required for the removal of either 3'-hydroxyl terminus protecting group W or 5'-hydroxyl terminus protecting group Y.

Phosphite compounds having formula IV can then be oxidized to produce compounds having formula V (n=1).

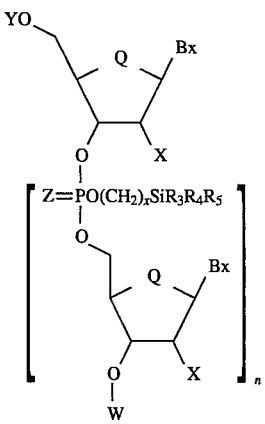

V

Such oxidation can be effected to both phosphodiester (Z=O) and phosphorothioate (Z=S) structures. Useful sulfurizing agents include Beaucage reagent described in e.g., Iyer, R. P.; Egan, W.; Regan, J. B.; Beaucage, S. L., 3H-1,2-Benzodithiole-3-one 1,1-Dioxide as an Improved Sulfurizing Reagent in the Solid-Phase Synthesis of Oligodeoxyribonucleoside Phosphorothioates, *Journal of American Chemical Society*, 1990, 112, 1253–1254 and Iyer, R. P.; Phillips, L. R.; Egan, W.; Regan J. B.; Beaucage, S. L., The Automated Synthesis of Sulfur-Containing Oligodeoxyribonucleotides Using 3H-,2-Benzodithiol-3-one 1,1-Dioxide as a Sulfur-Transfer Reagent, *Journal of Organic Chemistry*, 1990, 55, 4693–4699. Tetraethyl- thiuram disulfide can also be used as described in Vu, H.; Hirschbein, B. L., Internucleotide Phosphite Sulfurization With Tetraethylthiuram Disulfide, Phosphorothioate Oligonucleotide Synthesis Via Phosphoramidite Chemistry, *Tetrahedron Letters*, 1991, 32, 3005–3007. Further useful reagents for this step are dibenzoyl Tetrasulfide, Rao, M. V.; Reese, C. B.; Zhengyun, Z., Dibenzoyl Tetrasulphide—A Rapid Sulphur Transfer Agent in the Synthesis of Phosphorthioate Analogues of Oligonucleotides, *Tetrahedron Letters*, 1992, 33, 4839–4842; di(phenylacetyl)disulfide, Kamer, R. C. R.; Roelen, H. C. P. F.; van den Eist, H.; van der Marel, G. A.; van Boom, J. H., An Efficient Approach Toward the Synthesis of Phosphorothioate Diesters Va the Schonberg Reaction, *Tetrahedron Letters*, 1989, 30, 6757–6760; sulfur; and sulfur in combination with ligands like triaryl, trialkyl or triaralkyl or trialkaryl phosphines. Useful oxidizing agents include iodine/tetrahydrofuran/water/pyridine, hydrogen peroxide/water, tert-butyl hydroperoxide, or a peracid like m-chloroperbenzoic acid. In the case of sulfurization, reaction is performed under anhydrous conditions with the exclusion of air, in particular oxygen, whereas in the case of oxidation the reaction can be performed under aqueous conditions.

In certain embodiments, compounds having formula V are exposed to reaction conditions effective to remove the 5' hydroxyl protecting group Y, and the resultant product is contacted with additional monomer II to form phosphite oligonucleotides having formula VIII (n=1).

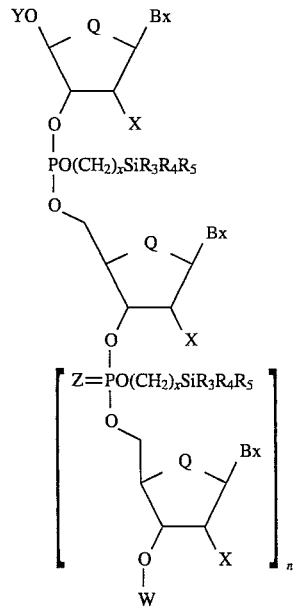

VIII

As will be recognized, further compounds having formula VIII, wherein Y and W are hydroxyl protecting groups and n is, for example, 2–200, can be prepared by oxidizing the phosphite intermediate to the phosphate, followed by removing the Y hydroxyl protecting group, and reacting with additional monomer II. It will further be recognized, that multiple iteration of this reaction can be effect to extend the oligonucleotide for increasing values of n.

In preferred embodiments, compound having formula IV are exposed to reaction conditions effective to remove the 5' hydroxyl protecting group Y, and reacting the resultant product is with additional monomer II to form phosphite oligonucleotides having formula IVb (n=2).

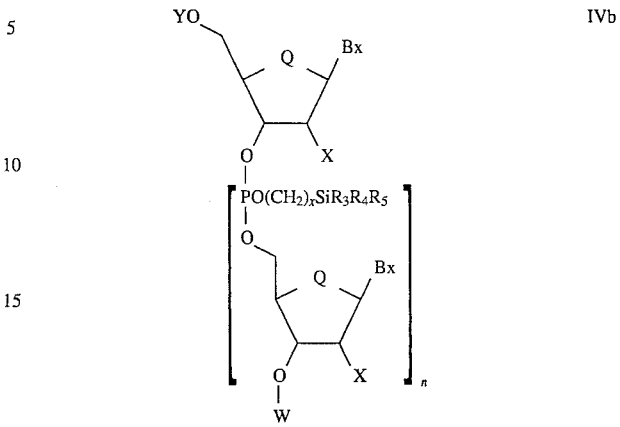

As will be recognized, further compounds having formula IVb, wherein W is a hydroxyl protecting group and n is, for example, 3–200, can be prepared by removing the 5'-hydroxyl protecting group Y and adding additional monomer of formula II.

Oxidation products having, for example, formula V can be exposed to conditions effective to cleave the 3'-OH protecting group W. The resulting product is contacted with ammonium hydroxide or some other aqueous base or fluoride ion to remove the silylalkyl portion thereof to yield phosphodiester and phosphorothioate-containing compounds having, for example, formula IX.

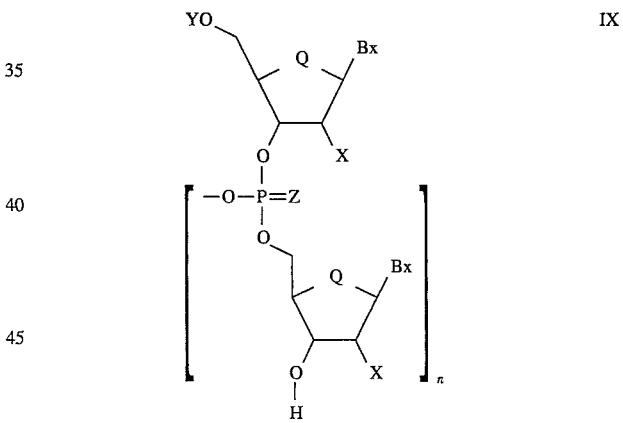

Contact with fluoride ion preferably is effected in a solvent such as tetrahydrofuran or acetonitrile or dimethoxyethane or water. Fluoride ion preferably is provided in the form of one or more salts selected from tetraalkylammonium fluorides (e.g., tetrabutylammonium fluoride (TBAF) or potassium fluoride or Cesium fluoride.

A more preferred method of removing the phosphorous protecting group is effected via the use of tetrafluorosilane in a "wet" solvent. Suitable as the solvent is acetonitrile having a trace of water. A 100:1 mixture gave essentially immediate deprotection at room temperature without any indication of cleavage of the internucleotide linkage. While we do not wish to be bound by theory, it is believed that this deprotection is effected via a β-fragmentation mechanism that is a result of coordination of the silicon atom of the tetrafluorosilane with the ether oxygen atom of the protecting group. Electron withdrawal at the ether oxygen atom is augmented by the electron withdrawing effects of the fluorine atoms of the tetrafluorosilane moiety.

The 3'-hydroxyl protecting group Y can be removed from compounds having, for example, formula IX by techniques well known in the art to produce compounds having formulas VI and VIa wherein Y is replaced by H. For example, dimethoxytrityl protecting groups can be removed by protic acids such as formic acid, dichloroacetic acid, trichloroacetic acid, p-toluene sulphonic acid or any other acid or with Lewis acids like zinc bromide or any other Lewis acid.

The 3'-hydroxyl protecting group W can be removed from compounds having, for example, formula IX by techniques well known in the art to produce compounds wherein W is replaced by H. For example, acetyl protecting groups can be removed by barium hydroxide.

In a preferred embodiment, compounds of the present invention are reacted in iterative fashion to produce oligonucleotides of up to about 200 units. A more preferred size is up to about 50 units. FIG. 1 is a reaction schematic depicting exemplary routes for the preparation of intermediates useful in the synthesis of oligonucleotides. 3'-O-Acetyl deoxythymidine is reacted with 5'-DMT DPSE phosphoramidite, monomer 2, and subsequently oxidized to form dimer 3, which has hydroxyl protecting groups at the 3'- and 5'-hydroxyl termini. Dimer 3 is then either deprotected at the 5'-hydroxyl to yield dimer 4, or deprotected at the 3'-hydroxyl and phosphitylated to produce activated dimer 5. 3'-O-Acetyl deoxyguanine is reacted with 5'-DMT DPSE phosphoramidite 6 and subsequently sulfurized, i.e. oxidized, to form dimer 7, which is then either deprotected at the 5'-hydroxyl to yield dimer 8, or deprotected at the 3'-hydroxyl and phosphitylated to produce activated dimer 9.

Figure 2:
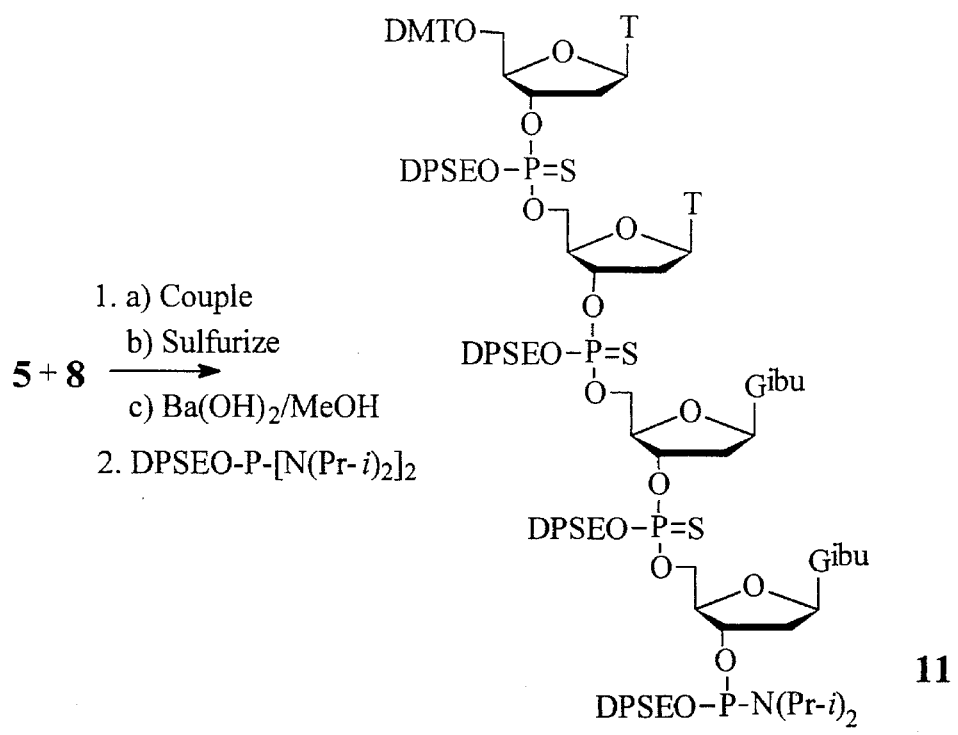
FIG. 2 is a schematic showing exemplary coupling of the intermediates of FIG. 1.
Figure 2:
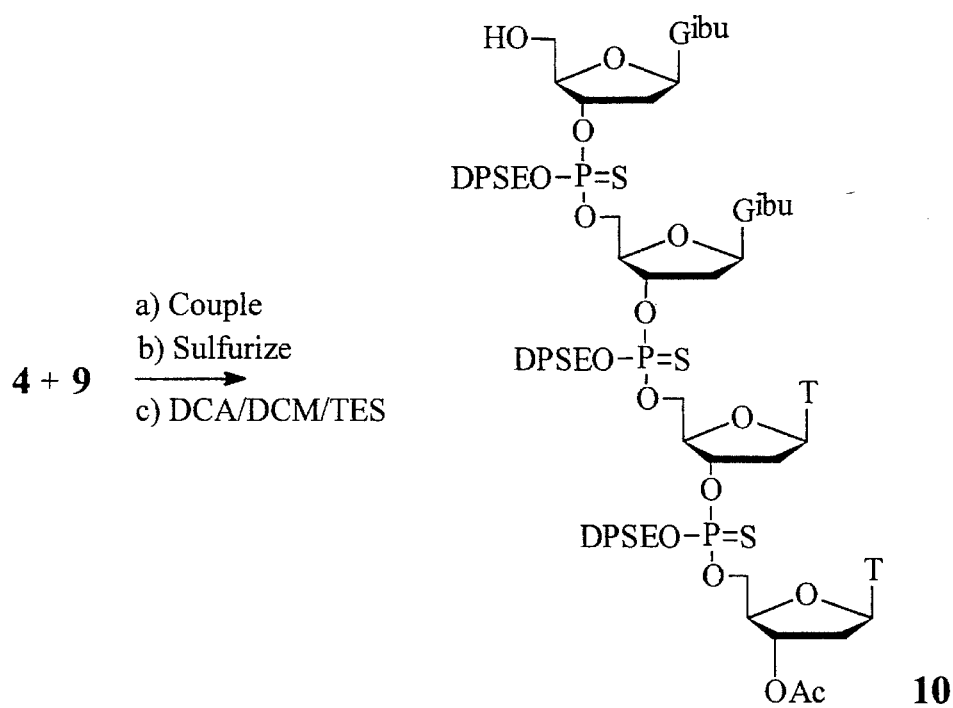

FIG. 2 shows the coupling of dimer 8 and activated dimer 5 and subsequent sulfurization, 3'-O-deactylation, and phosphitylation to yield activated tetramer 10. FIG. 2 also shows the coupling of dimer 4 and activated dimer 9 and subsequent sulfurization and 5'-hydroxyl deprotection to yield 3'-O-acetylated tetramer 11.

Figure 3:
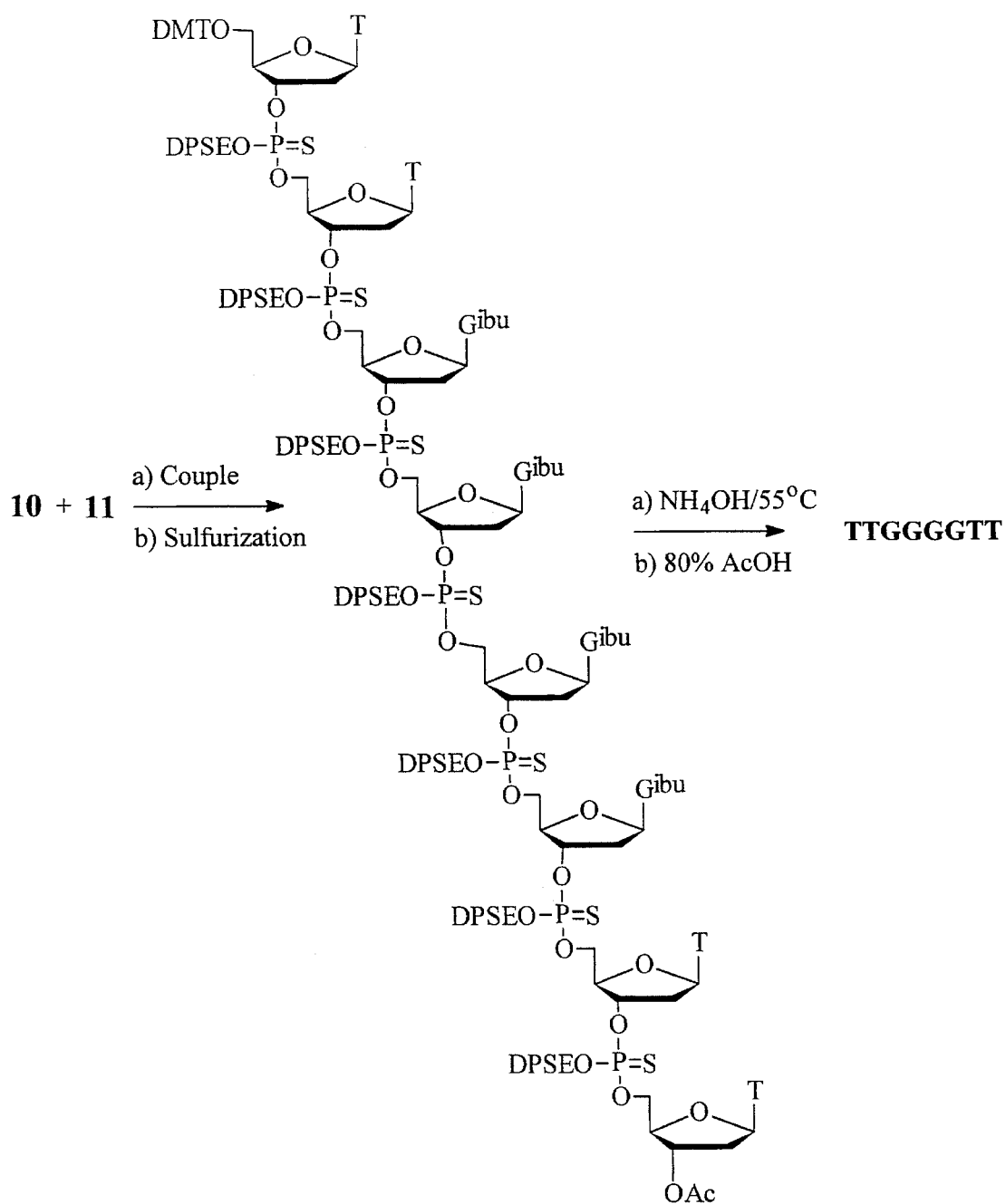
FIG. 3 depicts the coupling of the moieties of FIG. 2.

FIG. 3 shows the coupling and subsequent sulfurization of 3'-O-acetylated tetramer 11 and activated tetramer 10 to yield the fully protected octamer 12, and subsequent reaction removal all protecting groups to yield oligomer T—T—G—G—G—G—T—T. As will be recognized, oligomers containing odd numbers of nucleotide units may be synthesized by incorporating a monomer of formula II or another nucleosidic moiety containing an odd number of nucleoside subunits into the iterative process at any point in the process.

It will also be recognized that the processes of the invention may also be accomplished by reaction of a nucleotide containing a free hydroxyl at the 3'terminus with a nucleosidic moiety phosphitylated at the 5'-hydroxy terminus.

Additionally, it will be recognized that the process steps of the present invention need not be performed any particular number of times or in any particular sequence. Accordingly, products incorporating one or several functional groupings of the enumerated formulas may be constructed according to the invention. For example, the iterative oxidation of a growing oligonucleotide chain may be independently achieved with sulfurizing agents or oxidizing agents to yield oligomers containing both phosphate and phosphorothioate groups.

It will be further seen that by substitution of the alkylsilyl ethoxy group of the coupling reagent $(R_1R_2N)_2PO(CH_2)_xSiR_3R_4R_5$ the process of the present invention may be employed to make other phosphorous-substituted oligonucleotides. For example, substitution of one or more of the alkylsilylethoxy groups with methyl groups would result in a methylphosphite intermediate, capable of subsequent oxidation by the methods of the invention to yield an oligonucleotide containing one or more methyl phosphonate linkages. In a like manner, use of β-cyanoethyl phosphorous groups can be employed. Analogously, it may be seen that starting with a phosphorothioamidite, the process of the invention may be utilized to produce oligonucleotides containing one or more phosphorodithioate linkages.

Additional objects, advantages, and novel features of this invention will become apparent to those skilled in the art upon examination of the following example thereof, which are not intended to be limiting.

EXAMPLE 1

Preparation of Fully Protected TT Dimer

To a solution of 1.42 g (5.0 mmol) of 3'-acetyl thymidine and 0.35 g (4.0 retool) of 1-H Tetrazole in acetonitrile (60 mL) is added 5.50 g (6.0 retool) of 5'-O-(4,4'-dimethoxytrityl) thymidine-3'-O-(2-diphenylmethylsilylethyl N,N-diisopropylphosphoramidite in 40 mL acetonitrile. The reaction mixture is stirred at room temperature under argon for 0.5 h. A solution of 5.0 g (25 mmol) of 3H-1,2-benzodithiol-3-one 1,1-dioxide in acetonitrile is added as quickly as possible with vigorous stirring. The reaction mixture is stirred at room temperature for 20 minutes. The reaction mixture is then filtered and concentrated. The crude product is purified by flash chromatography on silica gel using ethyl acetate/hexane. 1% triethylamine is used during the purification. $^{31}$P-NMR (CDCl$_3$, ppm): 66.80, 67.07.

EXAMPLE 2

Preparation of Fully Protected GG dimer

To a solution of 3'-acetyl-$N^2$-isobutyryl-2'-deoxyguanosine (5.0 mmole) and 1-H Tetrazole (4.0 mmole) in acetonitrile (60 mL) is added 5.50 g (6.0 mmol) of $N^2$-Isobutyryl-5'-O-(4, 4'-dimethoxytrityl)-2'-deoxyguanosine-3'-O-(2-diphenylmethylsilylethyl N,N-diisopropylphosphoramidite) in acetonitrile (40 mL). The reaction mixture is stirred at room temperature under argon for 0.5 h. A solution of 5.0 g (25 mmole) of 3H-1,2-benzodithiol-3-one 1,1-dioxide in acetonitrile is added as quickly as possible with vigorous stirring. The reaction mixture is stirred at room temperature for 20 minutes. The reaction mixture is then filtered and concentrated. The crude product is purified by flash chromatography on silica gel using ethyl acetate/hexane. 1% Triethylamine is used during the purification. $^{31}$P-NMR (CDCl$_3$, ppm): 66.8, 67.1.

EXAMPLE 3

Preparation of the 5'-HO-TT Dimer

Fully protected phosphorothioate TT dimer (1 mmol) is dissolved in dichloromethane (50 mL) and 3% dichloroacetic acid in dichloromethane (v/v) (20 mL) is added and stirred for 15 minutes. The reaction mixture is concentrated and purified by flash chromatography on silica gel using ethyl acetate/hexane. 1% Triethylamine is used during the purification. $^{31}$P-NMR (CDCl$_3$, ppm): 67.3, 67.41.

EXAMPLE 4

Preparation of the 5'-HO-GG Dimer

Fully protected phosphorothioate GG dimer (1 mmol) is dissolved in dichloromethane (50 mL) and 3% dichloroacetic acid in dichloromethane (v/v) (20 mL) is added and stirred for 15 minutes. The reaction mixture is concentrated and purified by flash chromatography on silica gel using ethyl acetate/hexane. 1% Triethylamine is used during the purification. $^{31}$P-NMR (CDCl$_3$, ppm): 67.5, 67.6.

EXAMPLE 5

Preparation of Fully Protected TTT trimer

To a stirred solution of 5'-HO-TT phosphorothioate dimer (5.0 mmole) and 1-H Tetrazole (5.0 mmole) in acetonitrile (60 mL) is added 5'-O-(4,4'-dimethoxytrityl) thymidine-3'-O(2-diphenylmethylsilylethyl N,N-diisopropylphosphoramidite) (6.0 mmol) in acetonitrile (40 mL). The reaction mixture is stirred at room temperature under argon for 0.5 h. A solution of 3H-1,2-benzodithiol-3-one 1,1-dioxide (25 mmol) in acetonitrile is added as quickly as possible with vigorous stirring. The reaction mixture is stirred at room temperature for 20 minutes. The reaction mixture is then filtered and concentrated. The crude product is purified by flash chromatography on silica gel using ethyl acetate/hexane. 1% Triethylamine is sued during the purification.

EXAMPLE 6

Preparation of Fully Protected CTT trimer

To a solution of 5'-HO-TT phosphorothioate dimer (5.0 mmole) and 1-H Tetrazole (5.0 mmole) in acetonitrile (60 mL) is added N$^4$-Benzoyl-5'-O-(4,4'-dimethoxytrityl)-2'-deoxycytidine-3'-O- (2-diphenylmethylsilylethyl N,N-diisopropylphosphoramidite) (6.0 mmol) in acetonitrile (40 mL). The reaction mixture is stirred at room temperature under argon for 0.5 h. A solution of 3H-1,2-benzodithiol-3-one 1,1-dioxide (25 mmol) in acetonitrile is added as quickly as possible with vigorous stirring. The reaction mixture is stirred at room temperature for 20 minutes. The reaction mixture is then filtered and concentrated. The crude product is purified by flash chromatography on silica gel using ethyl acetate/hexane. 1% Triethylamine is used during the purification.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the solution phase preparation of an oligonucleotide comprising reacting, in solution, a first synthon having the structure

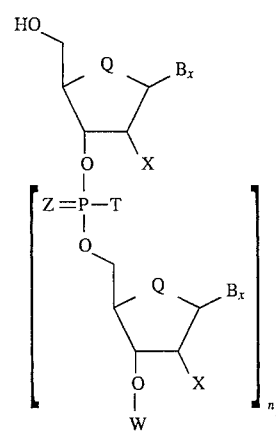

with a second synthon having the structure

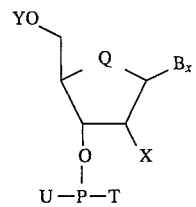

to form a moiety having the structure

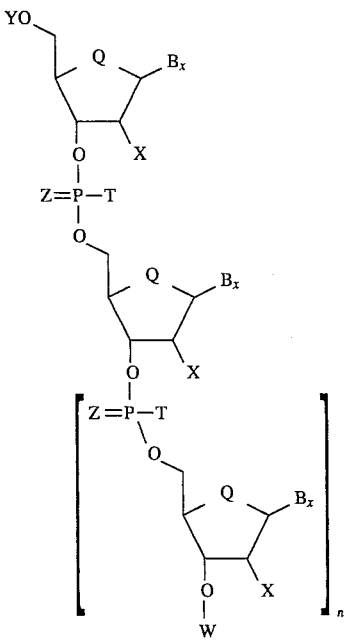

where each Q is independently O or S;
each B$_x$ is independently a nucleosidic base;
each X is independently, H, OH, F, O-alkyl, S-alkyl, N-alkyl, O-alkenyl, S-alkenyl or N-alkenyl;
each Y is independently a 5' hydroxyl protecting group;
W is a 3' hydroxyl protecting group;
each Z is independently O or S;
each T is independently —O—(CH$_2$)$_x$SiR$_3$R$_4$R$_5$;
R$_3$, R$_4$ and R$_5$ are each independently alkyl or aryl;

U is a phosphite activating group;

n is an integer from 0 to 50; and x is 1 to about 7.

2. The process of claim 1 wherein $R_3$, $R_4$ and $R_5$ are selected from the group consisting of methyl or phenyl.

3. The process of claim 1 wherein U is a dialkylamino group.

4. The process of claim 1 wherein said second synthon is formed by reacting a reagent $(R_1R_2N)_2PO(CH_2)_xSiR_3R_4R_5$, wherein $R_1$ and $R_2$ independently are alkyl having 1 to about 10 carbon atoms, and $R_3$, $R_4$, and $R_5$ are, independently, alkyl having 1 to about 10 carbon atoms or aryl having 6 to about 10 carbons atoms, and x is 1 to about 7; with a nucleoside to form said second synthon.

5. The process of claim 4 wherein the reaction takes place in the presence of 1H-tetrazole, 5-(4-nitrophenyl)-1H-tetrazole, or diisopropylammonium tetrazolide.

6. The process of claim 1 further comprising removing one or more of the members selected from the group consisting of W, T or Y from the oligonucleotide and oxidizing the oligonucleotide to form phosphorothioate or phosphodiester internucleoside linkages.

7. The process of claim 6, comprising removing Y to form a first synthon for iterative reaction with a further second synthon.

8. The process of claim 6, comprising removing W to form a second synthon for iterative reaction with a further first synthon.

9. A method for preparing an oligomer comprising reacting together, in solution, a first synthon comprising at least two nucleoside units and having a 5' location protected with a 5' hydroxylic blocking group and a 3' location substituted with a function having the formula

U—P—T wherein U is a phosphite activating group and T is —O—$(CH_2)_x SiR_3R_4R_5$ wherein $R_3$, $R_4$ and $R_5$ are each independently alkyl or aryl, and x is 1 to about 7, with a second synthon comprising a nucleoside unit having a 3' location protected with a 3' hydroxylic blocking group and a 5' location capable of reacting with the U—P—T function.

10. The method of claim 9 wherein the product of the reaction is oxidized to form either phosphate or phosphorothioate internucleoside bonds.

11. The method of claim 9 wherein said second synthon comprises at least two nucleoside units.

12. The method of claim 9 wherein the function U—P—T is incorporated through reaction with a reagent $(R_1R_2N)_2PO(CH_2)_xSiR_3R_4R_5$ wherein $R_1$ and $R_2$ independently are alkyl having 1 to about 10 carbon atoms, $R_3$, $R_4$, and $R_5$ are, independently, alkyl having 1 to about 10 carbon atoms or aryl having 6 to about 10 carbons atoms, and x is 1 to about 7.

13. A compound having one of the formulas

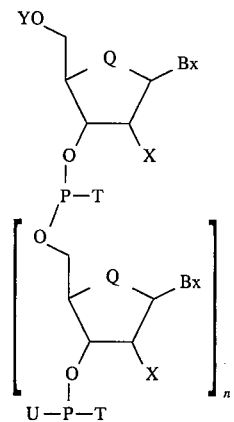

or

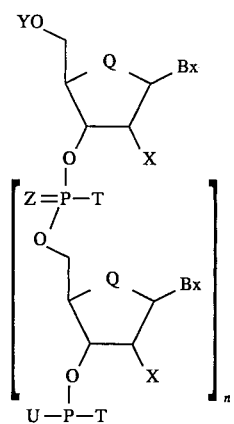

where each Q is independently O or S;

each $B_x$ is independently a nucleosidic base;

each X is independently, H, OH, F, O-alkyl, S-alkyl, N-alkyl O-alkenyl, S-alkenyl or N-alkenyl;

each Z is independently O or S;

Y is H or a hydroxyl protecting group;

U is a phosphite activating group;

each T is independently —O—$(CH_2)_xSiR_3R_4R_5$;

$R_3$, $R_4$ and $R_5$ are each independently alkyl or aryl;

n is an integer from 0 to 200; and x is 1 to about 7.

14. The compound of claim 13 wherein Q is O.

15. The compound of claim 13 wherein X is H, OH or O-alkyl.

16. The compound of claim 13 wherein T has the formula —O$(CH_2)_xSiR_3R_4R_5$ wherein $R_3$, $R_4$, and $R_5$ are, independently, alkyl having 1 to about 10 carbon atoms or aryl having 6 to about 10 carbons atoms, and x is 1 to about 7.

* * * * *

UNITED STATES PATENT AND TRADEMARK OFFICE
CERTIFICATE OF CORRECTION

PATENT NO. : 5,571,902
DATED : November 5, 1996
INVENTOR(S) : Vasulinga Ravikumar, Douglas L. Cole It is certified that error appears in the above-indentified patent and that said Letters Patent is hereby corrected as shown below:

Column 20, Line 20, please delete "retool" and insert "mmol"

Column 20, lines 21, please delete "retool" and insert "mmol"

Signed and Sealed this

Twenty-ninth Day of April, 1997

Attest:

BRUCE LEHMAN

*Attesting Officer*   *Commissioner of Patents and Trademarks*